United States Patent [19]
Alexandratos

[11] Patent Number: 5,990,336
[45] Date of Patent: Nov. 23, 1999

[54] SYNTHESIS AND PURIFICATION OF ZOSTERIC ACID

[75] Inventor: Spiro D. Alexandratos, Knoxville, Tenn.

[73] Assignee: The University of Tennessee Research Corporation, Knoxville, Tenn.

[21] Appl. No.: 08/782,106

[22] Filed: Jan. 13, 1997

[51] Int. Cl.$^6$ .................................................. C07C 305/00
[52] U.S. Cl. ............................................. 558/37; 562/429
[58] Field of Search ................................ 558/37; 562/429

[56] References Cited

U.S. PATENT DOCUMENTS

| | | | |
|---|---|---|---|
| 3,549,562 | 12/1970 | Mindick et al. | 260/2.1 |
| 3,843,566 | 10/1974 | Barrett | 260/2.1 |
| 4,224,415 | 9/1980 | Meitzner et al. | 521/38 |
| 5,312,977 | 5/1994 | Yanaka et al. | 562/443 |
| 5,384,176 | 1/1995 | Zimmerman et al. | 428/68 |
| 5,472,966 | 12/1995 | Sloan et al. | 514/255 |

OTHER PUBLICATIONS

Alexandratos, et al., "Metal Ion Extraction Capability of Phosphinic Acid Resins: Comparative Study of Phosphinic, Sulfonic, and Carboxylic Resins Using Zinc Ions", Macromolecules, vol. 18, No. 5 pp. 835–840 (1985).

Alexandratos, et al., "Synthesis and Characterization of Bifunctional Phosphinic Acid Resins", Macromolecules, vol. 18, No. 5 pp. 830–835 (1985).

Vassilev, et al., "Microsynthesis of Some Hydroxycinnamic Acids and a Study of Their Metabolism in Plants", Tome 34, No. 7, pp. 125–128 (1981).

*Primary Examiner*—Paul J. Killos
*Attorney, Agent, or Firm*—Morgan, Lewis & Bockius LLP

[57] ABSTRACT

The synthesis and purification of zosteric acid is described. The specification describes methods for preparing p-coumaric acid, for preparing zosteric acid, and purifying zosteric acid. Zosteric acid is prepared from p-coumaric acid. Zosteric acid, however, need not be prepared by any particular method to be purified by a method of the invention. All three methods may be used in combination to prepare and purify zosteric acid.

16 Claims, No Drawings

SYNTHESIS AND PURIFICATION OF ZOSTERIC ACID

FIELD OF THE INVENTION

Zosteric acid has been shown to control biofouling of surfaces in contact with marine environments. The present invention relates to the synthesis and purification of zosteric acid. More particularly, the present invention relates to a method for the preparation of p-coumaric acid; to a method for the preparation of zosteric acid; and to a method for the purification of zosteric acid.

BACKGROUND OF THE INVENTION

Surfaces in contact with marine environments (which include fresh water, brackish water and salt water environments) are known to become fouled by various types of organisms, both microorganisms and macro organisms. Vulnerable surfaces include, for example, the hulls of ships or the inside of pipes in circulating or pass-through water systems. Attaching themselves to these surfaces, organisms not only impede water flow across the surface hampering performance, but can also cause deterioration of the surface itself. As one example, Zebra mussels, which have relatively recently entered the Great Lakes, have been known to accumulate on and foul ship hulls and the water intake systems of power plants. Removing Zebra mussels takes ships or plant equipment out of service causing costly delays, repair, and cleanup. A need exists, therefore, for chemicals which combat biofouling and alleviate its adverse economic costs. Safety concerns, however, require that any such chemical should not pose undue harm to the environment or humans.

U.S. Pat. No. 5,384,176 describes the use of zosteric acid (p-sulfoxycinnamic acid) to control biofouling on surfaces in contact with marine environments. Zosteric acid is reported not only to be effective in combating biofouling but also to be environmentally safe. Zosteric acid occurs naturally in eelgrass *Zostera marina*. U.S. Pat. No. 5,384,176 discloses a method for isolating zosteric acid from methanolic extracts of eelgrass.

Extracting zosteric acid from eelgrass, however, can often be an expensive, time consuming processes with varying yields. If zosteric acid is to be a viable chemical to combat biofouling, there needs to be a synthetic route for its preparation and purification. The present invention answers that need by providing methods for the preparation of zosteric acid and its precursor, p-coumaric acid. The present invention also provides a method for purifying zosteric acid. These processes supply zosteric acid in good yield and high purity.

SUMMARY OF THE INVENTION

One embodiment of the invention relates to a method for the preparation of p-coumaric acid. The method combines malonic acid, p-hydroxy benzaldehyde, and aniline in pyridine to form a reaction mixture. The molar ratio of the malonic acid to the p-hydroxy benzaldehyde is about 2:1 and the molar ratio of aniline ranges from 0.05 to 0.2 moles aniline per mole of p-hydroxy benzaldehyde. The reaction mixture is heated to a temperature ranging from about 40 to 80° C. and allowed to react for a time sufficient to form p-coumaric acid.

Another embodiment relates to a method for preparing zosteric acid. This method dissolves p-coumaric acid in pyridine to yield a solution, adds chlorosulfonic acid to the pyridine solution, and then allows the p-coumaric acid and chlorosulfonic acid to react for a time and under conditions sufficient to form zosteric acid. Sufficient water is then added to hydrolyze any remaining chlorosulfonic acid. The resulting solution is extracted with a water-immiscible, polar organic solvent to yield an aqueous phase and an organic phase which are then separated. Removing water from the separated aqueous phase yields solid zosteric acid.

A further embodiment of the invention provides a method for purifying zosteric acid. This method contacts a material containing zosteric acid with water under conditions sufficient to substantially dissolve the zosteric acid forming an aqueous solution containing zosteric acid and adds an amount of a strong Brönsted base to the aqueous solution to neutralize the zosteric acid and form a basic solution containing a zosteric acid salt. Extracting the basic solution with a water-immiscible, polar organic solvent to yield an aqueous phase and an organic phase. The aqueous phase is separated from the organic phase and the water removed from the aqueous phase to yield a solid containing the zosteric acid salt. The solid containing the zosteric acid salt is redissolved in water to form an aqueous solution containing the zosteric acid salt which is then acidified to convert the zosteric acid salt to zosteric acid. Removing the water from the acidified aqueous solution yields a solid containing zosteric acid which is then dissolved in methanol. Any undissolved solid is removed from the methanol solution before the methanol is removed from the methanol solution to yield another solid containing zosteric acid. This solid containing zosteric acid is dissolved in water to form an aqueous solution containing zosteric acid which is passed through a crosslinked, strongly basic anionic exchange resin in its hydroxyl form and then through a crosslinked, strongly acidic ion exchange resin. Removing the water from the aqueous solution containing zosteric acid yields solid zosteric acid.

Advantageously, the various embodiments of the invention may be combined in a synthetic scheme to prepare zosteric acid ultimately from p-hydroxy benzaldehyde. The zosteric acid is obtained in high purity and good yield. The various embodiments of the invention are discussed in more detail below.

DETAILED DESCRIPTION OF THE INVENTION

The present invention relates to the synthesis and purification of zosteric acid. According to the invention, zosteric acid is prepared from p-coumaric acid. The invention provide methods for preparing p-coumaric acid, for preparing zosteric acid, and purifying zosteric acid. Zosteric acid need not be prepared by any particular method to be purified by a method of the invention. A preferred embodiment of the invention, employs all three methods to prepare and purify zosteric acid.

According to the invention, p-coumaric acid is prepared by combining malonic acid, p-hydroxy benzaldehyde, and aniline in pyridine. This forms a reaction mixture where the pyridine acts as a solvent. The malonic acid, p-hydroxy benzaldehyde, and aniline may be added together or separately. The malonic acid is preferably dissolved in the pyridine prior to adding the p-hydroxy benzaldehyde and aniline to form a reaction mixture. The reaction mixture is stirred, or otherwise agitated, to ensure the malonic and the p-hydroxy benzaldehyde mix well and, preferably, dissolve in the pyridine. Preferably enough pyridine is used to fully dissolve the malonic acid and p-hydroxy benzaldehyde.

The molar ratio of the malonic acid to the p-hydroxy benzaldehyde in the reaction mixture is about 2:1. In a preferred embodiment, a slight excess of malonic acid may be used. The amount of aniline may range from 0.05 to 0.2 moles per mole of p-hydroxy benzaldehyde. Preferably, the amount of aniline ranges from about 0.1 to 0.15 moles per mole of p-hydroxy benzaldehyde, and more preferably about 0.1 moles.

The reaction mixture is heated to a temperature ranging from about 40 to 80° C. and allowed to react for a time sufficient to form p-coumaric acid. Preferably, the reaction mixture is heated to about 60 to 70° C., and most preferably about 65° C. In a preferred embodiment, the aniline is added to the heated reaction mixture. Generally, the reaction mixture may be stirred for about eight hours to allow complete reaction. The reaction may be monitored by standard techniques such as liquid chromatography or infrared spectroscopy.

After the reaction is complete, the pyridine and aniline are neutralized by adding a strong Brönsted acid to the reaction mixture. Because the neutralization reaction is generally exothermic, the reaction mixture may be cooled to room temperature or below prior to adding the acid. Sufficient acid should be used to fully neutralize the pyridine and aniline. A slight excess may be employed. The acid is generally added dropwise as an aqueous solution. Any strong acid, such as hydrochloric acid or sulfuric acid, may be used for this neutralization. A 2 N aqueous HCl solution is preferred.

Advantageously, using aniline according to the invention, the p-coumaric acid precipitates as a creamy white solid following the neutralization. In contrast, Vassilev, reporting synthesis of various hydroxycinnamic acids using a piperidine/pyridine reaction media, does not report any precipitation but utilizes multiple extractions to isolate the hydroxycinnamic acid product. See Vassilev et al., Comptes rendus de l'Académie bulgare des Sciences, Tome 34, No. 7, 1981, pp. 125–28. In a method of the invention, precipitation may begin during the neutralization step. The precipitated p-coumaric acid may be collected using techniques known in the art, such as filtration or centrifugation. The p-coumaric acid obtained from a method of the invention generally has a purity ≧95%.

The p-coumaric acid from the above synthesis may then be used to prepare zosteric acid, another embodiment of the invention. Though any p-coumaric acid may be used to prepare zosteric acid according to the invention, p-coumaric acid prepared as described above is preferred, particularly when combining the preparation of p-coumaric and zosteric acid in a single procedure.

In a method to prepare zosteric acid according to the invention, p-coumaric acid is dissolved in pyridine to yield a pyridine solution. The pyridine solution may then be cooled to about e.g., about −5° C. to about 5° C., preferably about 0° C.

Chlorosulfonic acid is added to the pyridine solution to form a reaction mixture. Preferably, the chlorosulfonic acid is added dropwise while maintaining the cooled temperature. About 1 mole of chlorosulfonic acid per mole of coumaric acid may be used. A slight excess is acceptable. Due to the reaction's exothermic nature, the reaction mixture is preferably stirred at the cooled temperature, e.g., about 0° C., for a time sufficient to allow the p-coumaric acid and the chlorosulfonic acid to react and form zosteric acid. Preferably, the reaction mixture is stirred for about 2 to about 4 hours at the low temperature, more preferably about 2.5 to about 3 hours.

The reaction mixture may then be heated to a temperature ranging from about 40° C. to about 60° C. and allowed to react at that temperature for a time sufficient to form zosteric acid. This pushes the reaction between the p-coumaric acid and the chlorosulfonic acid to completion. Preferably, the reaction mixture is heated to about 45° C. and stirred for about 10 to about 20 hours, more preferably about 15 hours. The reaction may be monitored by standard techniques such as chromatography, e.g., liquid chromatography, or spectroscopy, e.g., IR spectroscopy.

After the reaction is complete, sufficient water is added to the reaction mixture to hydrolyze the chlorosulfonic acid. Because the hydrolysis is generally exothermic, the reaction mixture may be cooled to about −5° C. to about 5° C., preferably about 0° C. Preferably added dropwise, sufficient water should be used to completely hydrolyze the chlorosulfonic acid. Generally, the amount of water added may equal or exceed the amount of pyridine used. Preferably, one to one and half times the amount of pyridine may be used.

The resulting solution is then extracted with an organic solvent forming two separate phases, an organic phase and an aqueous phase. The aqueous phase, containing the zosteric acid, is separated from the organic phase and retained. Any water-immiscible, polar organic solvent capable of removing unwanted organic by-products and forming a distinct organic phase may be used. A preferred water-immiscible, polar organic solvent is diethyl ether. The aqueous phase may be extracted multiple times to further purify the zosteric acid. Preferably, the aqueous phase is extracted at least twice with diethyl ether.

Removing the water from the separated aqueous phase yields a solid material containing zosteric acid. The water may be removed using techniques known in the art. For example, the water may be removed by evaporation, particularly under reduced pressure. Preferably, the water is removed by rotovapping the separated aqueous phase. In a preferred embodiment, the aqueous phase, without removing the water, is carried directly into the method for purifying zosteric acid according to the invention.

The present invention zosteric acid also relates to a method for purifying zosteric acid. The zosteric acid may be prepared by the above method or obtained from natural sources such as eelgrass as disclosed in U.S. Pat. No. 5,384,176. To obtain purified zosteric acid, a material containing zosteric acid is combined with water under conditions sufficient to substantially dissolve the zosteric acid. This forms an aqueous solution containing the zosteric acid. Any undissolved solids may be removed from the aqueous solution by means known in the art such as filtration or centrifugation.

A strong Brönsted base is then added to the aqueous solution to neutralize the zosteric acid and form its corresponding salt. Preferably, sufficient base should be added to obtain a basic solution having a pH of about 9–11. The final pH is preferably about 10. Any strong Brönsted base may be used in this neutralization step. For example, bases such as sodium hydroxide, potassium hydroxide, or calcium hydroxide may be used. Sodium hydroxide is preferred and yields a sodium salt of zosteric acid The base is preferably added as an aqueous solution. A 10 N aqueous solution of NaOH may be used. This neutralization steps yields a basic solution which is carried forward in the purification.

The basic solution is then extracted with a water-immiscible, polar organic solvent forming two separate phases, an organic phase and an aqueous phase. This extraction step may be performed in the same manner as discussed above. The aqueous phase, containing the zosteric acid salt, is separated from the organic phase and retained. As above, any water-immiscible, polar organic solvent capable of removing unwanted organic by-products and forming a distinct organic phase may be used. A preferred water-immiscible, polar organic solvent is diethyl ether. The aqueous phase may be extracted multiple times to further purify the zosteric acid salt. Preferably, the aqueous phase is extracted at least twice with diethyl ether.

Removing the water from the separated aqueous phase yields a solid containing the zosteric acid salt. The water may be removed using techniques known in the art. For example, the water may be removed by evaporation, preferably under reduced pressure and/or at elevated temperature. Preferably, the water is removed by lyophilizing or rotovapping the separated aqueous phase to yield the solid.

The solid containing the zosteric acid salt is redissolved in water and acidified to convert the zosteric acid salt to zosteric acid. Undissolved solids may be removed before acidification by, for example, filtering or centrifuging, the aqueous solution. Sufficient acid should be added to convert the zosteric acid salt to its acid form and reach pH 7. A slight excess of acid may be employed. Cooling may be used if the acidification is exothermic. The acid is generally added dropwise as an aqueous solution. Any strong acid, such as hydrochloric acid or sulfuric acid, may be used for this neutralization. A 2 N aqueous HCl solution is preferred. In an alternative embodiment, the separated aqueous phase from the extraction step may be acidified directly rather than isolating the solid and redissolving it in water for acidification.

After the acidification step, the water may be removed to yield a solid, containing zosteric acid and salts from the acidification. The water may be removed using techniques known in the art. For example, as discussed above, the water may be removed by evaporation, preferably under reduced pressure and/or at elevated temperature. Preferably, the water is removed by lyophilizing or rotovapping the separated aqueous phase to yield the solid. The solid may be further dried using standard techniques.

The solid resulting from the acidification step is dissolved in methanol to give a methanol solution. Dissolving the solid in the methanol reduces the concentration of salts in contact with the zosteric acid. Any undissolved solid material, such as a salt, may be removed from the methanol solution by means known in the art such as filtration or centrifugation.

The methanol is then removed from the methanol solution to yield a second solid, containing the zosteric acid and salts at a lower level than initially. The methanol may be removed using techniques known in the art. Preferably, the alcohol is removed by evaporation and more preferably by evaporation under reduced pressure, such as by rotovapping.

The solid recovered from the methanol solution is dissolved in sufficient water to form an aqueous solution of zosteric acid. As discussed above, any undissolved solid may be removed by known techniques.

To separate remaining contaminants, such as salts, from the zosteric acid, the aqueous solution is passed through a crosslinked, strongly basic anionic exchange resin in its hydroxyl form and then through a crosslinked, strongly acidic cationic exchange resin. The exchange resins combine both size exclusion and ion exchange to remove contaminants from the zosteric acid. The aqueous solution containing the zosteric acid may be passed through separate columns of the anionic and cationic exchange resins or a single column containing the anionic and cationic resins in series. In a single column, a plug of inert material, such as sand or silica, may be used to separate the resins.

The anionic exchange may, for example, be a styrene-based resin having ammonium groups, preferably trimethyl ammonium groups. The cationic exchange resin may, for example, be a styrene-based resin having carboxylic acid or, preferably, sulphonic acid groups. U.S. Pat. Nos. 3,459,562 and 4,224,415 describe the preparation of such anionic and cationic exchange resins. The disclosure of those patents is incorporated here by reference. See also Alexandratos et al., Macromolecules, 1995, 18, 829 and Macromolecules, 1995, 18, 825. Suitable exchange resins may also be obtained from Sybron Chemicals Inc., Birmingham, N.J.

In general, the anionic exchange resin and the cationic exchange resin should be sufficiently crosslinked to permit any contaminant, such as salt ions, to be removed while not trapping the zosteric acid within the resin matrix. In general, the resins may be 8–25% crosslinked with divinylbenzene. Preferably, the anionic exchange resin may be 10–25% crosslinked, and more preferably about 12% crosslinked when the contaminating anion is chloride. The cationic exchange resin is preferably, 10–20% crosslinked and more preferably about 10% crosslinked. The resins should preferably be a 40–60 mesh resins with a preferred porosity of about 20–60%. Larger mesh sizes may also be used. For the anionic exchange resin, a more preferred porosity is about 50%. And, for the cationic exchange resin, a porosity of 30% is more preferred.

The aqueous solution, or eluent, passing through each resin is collected. The resin may then be washed with sufficient water to ensure substantially no zosteric acid remains on the resin. When separate columns are used for each resin, the eluent and washes are preferably combined and carried forward in the purification process. If desired the volume of the combined eluent and washes may be reduced using the techniques described above to remove water from the various aqueous solutions.

After passing the aqueous solution containing the zosteric acid through the anionic and cationic exchange resins, the water is removed to yield purified solid zosteric acid. The water may be removed using techniques known in the art. For example, the water may be removed by evaporation, particularly under reduced pressure. Preferably, the water is removed by rotovapping the aqueous solution to obtain the zosteric acid. The zosteric acid purified from the process is generally $\geq 95\%$ pure. In a preferred embodiment, when the preparation of p-coumaric acid, the preparation of zosteric acid, and the purification of the zosteric acid are combined into a single procedure, the overall yield of zosteric acid is 50% or greater based on the malonic acid.

The following examples depict the various methods of the invention. These examples are intended to illustrate, not limit, the present invention.

EXAMPLE 1

Typical Synthesis of Anionic and Cationic Exchange Resins

Copolymer Synthesis. Vinylbenzene chloride/divinylbenzene (VBC/DVB) copolymer beads are synthesized by suspension polymerization as described in U.S. Pat. No. 3,843,566. In a typical preparation, gelatin (0.96 g), poly(diallyldimethylammonium chloride) (11.90 g, Calgon Corp.), and boric acid (6.33 g) are dissolved in 316.5 mL of $H_2O$. The pH is adjusted to 10.3 with 50% NaOH. The aqueous phase is poured into a 1-L round-bottom flask equipped with a condenser, dry nitrogen purge, a thermometer to which is attached a Therm-O-Watch temperature-control device (Instruments for Research and Industry, Cheltenham, Pa.), and an Eberbach Con-Torque stirrer with double-paddle stir shaft. The monomer mix is then added (420.1 g of VBC (Aldrich), 10.3 g of technical DVB (Dow Chemical Co.; analyzed to be 55.4% m- and p-DVB) for 2% cross-linking, and 3.00 g of benzoyl peroxide); the stir speed is set at 250 rpm. The suspension is heated over a 2-h period to 80° C. and the temperature held for 10 h. Complete polymerization is ensured by heating the system at 100° C. for 2 h. The beads are then washed 4 times with water and dried. MR beads are synthesized by replacing half the monomer mix with 4-methyl-2-pentanol (Aldrich) and adjusting the stir rate to 200 rpm. A 6 h steam distillation to remove the alcohol replaced the 2 h finish-off employed with gel synthesis.

Polymer-Supported Cation Exchange Resin. VBC/DVB copolymer beads are synthesized as described above. VBC/DVB copolymer beads (10 g) are swollen in toluene, added to 400 mL of alcoholic KOH (25 wt %) in a 500-mL round-bottom flask and refluxed for 24 h. The beads are then separated, washed 4 times with EtOH, and eluted with water until no longer basic. The beads are suction-dried and placed in a 500 mL round-bottom flask with 400 mL of concentrated $HNO_3$ and kept at 30° C. for 24 h. The beads are washed sequentially with 250 mL of 10, 5, 1, and 0.1 M $HNO_3$. The resin is then washed with water and conditioned with 1 L of $H_2O$, 1 N NaOH, $H_2O$, 1 N HCl, and $H_2O$, each with 1 h elution times. Alternatively, 10 g of crosslinked polystyrene beads are contacted with 100 ml concentrated sulfuric acid and refluxed for 17 h. The beads are washed with 50% $H_2SO_4$, then water, then conditioned as before.

Polymer-Supported Anion Exchange Resin. To 10 grams of the copolymer prepared with vinylbenzyl chloride, add 250 ml of aqueous trimethylamine (25 wt % solution). Reflux 4–17 h. Cool. Wash with water. Condition with 1 L $H_2O$, 4 wt % of NaOH, $H_2O$ to place resin in the preferred hydroxide form.

EXAMPLE 2

Preparation of Coumaric Acid

Malonic acid, 813 g, was added to p-hydroxy benzaldehyde, 472 g, in pyridine, 957 ml. The mixture was heated to 65° C. and aniline, 28 ml, was added. The reaction was stirred at 65° C. for 7.5 hours and then cooled to room temperature. HCl, 2.75 L, 2N HCl, was then added dropwise while the reaction stirred A creamy precipitate formed. The reaction was stirred for an additional 10 minutes. The precipitate was collected by filtration and dried under reduced pressure. The solid was identified as coumaric acid by IR spectroscopy. The yield was ≧80%.

EXAMPLE 3

Preparation and Purification of Zosteric Acid

Para-coumaric acid, 100 g prepared according to Example 1, was dissolved in pyridine, 400 ml. The pyridine solution was cooled to 0° C. and chlorosulfonic acid, 100 ml, was added dropwise over 3 hours. After stirring for 2.5 hours at 0° C., the reaction was heated to 46° C., stirred for an additional 15 hours, and then cooled to 0° C. Water, 500 ml, was then added dropwise. The resulting mixture was stirred for an additional 10 minutes after the water was added. The mixture was then extracted twice with diethyl ether, 500 ml each, and the aqueous phase retained.

The aqueous phase was then neutralized and taken to a pH of 10 by adding 10 N NaOH, about 500 ml. This pH 10 solution was then extracted four times with diethyl ether, 200 ml each. Again the aqueous phase was saved and the water removed by rotovapping to yield a solid. The solid was dissolved in water 150 ml, and neutralized to pH 7 with 1N HCl. The water was then removed by rotovapping to yield a solid. This second solid was dissolved in methanol, 300 ml. The undissolved solid was separated from the solution by centrifuging the solution and collecting the supernatant liquid. Rotovapping the supernatant liquid removed the methanol to yield a solid.

The solid was then dissolved in water, 2.5 g solid in 100 ml $H_2O$, and passed through a strong base ion-exchange resin, 42 g (approximately 12% crosslinked with divinylbenzene prepared as described in Example 1), in its hydroxide form. The eluent was collected and the resin washed with water, 500 ml. After combining the aqueous eluent and washing portions, the combined aqueous solutions was passed through a strong acid ion-exchange resin, 40 g (approximately 10% crosslinked with divinylbenzene, prepared as described in Example 1), and the eluent collected. The acid ion-exchange resin was washed with water, 100 ml. The aqueous eluent and washes were combined. The water was removed from the combined aqueous solution by rotovapping to yield a solid, zosteric acid. Overall yield 50% starting from Example 1 with a 95% purity. The purity was confirmed by chlorine elemental analysis and by infrared spectroscopy.

The claimed invention is:

1. In a method for preparing zosteric acid involving dissolving p-coumaric acid in pyridine to yield solution, adding chlorosulfonic acid to the pyridine solution, allowing the p-coumaric acid and chlorosulfonic acid to react for a time and under conditions sufficient to form zosteric acid, wherein the improvement comprises:

adding sufficient water to hydrolize any remaining chlorosulfonic acid;

extracting the solution with a water-immiscible, polar organic solvent to yield an aqueous phase and an organic phase;

separating the aqueous phase from the organic phase; and removing the water from the separated aqueous phase to yield solid zosteric acid.

2. A method of claim 1, further comprising the steps of:

after dissolving p-coumaric acid in pyridine to yield a solution, cooling the solution to about −5 to 5° C.;

after allowing the p-comaric acid and cholorsufonic acid to react at the cooled temperature, heating the solution to about 40 to 60° C. for a time sufficient to ensure complete reaction; and cooling the solution to about −5 to 5° C. before hydrolyzing with water.

3. A method of claim 2, wherein the water-immiscible, polar organic solvent is diethylether.

4. A method for purifying zosteric acid comprising the steps of:

contacting a material containing zosteric acid with water under conditions sufficient to substantially dissolve the zosteric acid forming an aqueous solution containing zosteric acid;

adding an amount of a strong Brönsted base to the aqueous solution containing the zosteric acid to neutralize the zosteric acid and form a basic solution containing a zosteric acid salt;

extracting the basic solution with a water-immiscible, polar organic solvent to yield an aqueous phase and an organic phase;

separating the aqueous phase from the organic phase;

removing the water from the aqueous phase to yield a solid containing the zosteric acid salt;

redissolving the solid containing the zosteric acid salt in water to form an aqueous solution containing the zosteric acid salt;

acidifying the aqueous solution containing the zosteric acid salt to convert the zosteric acid salt to zosteric acid;

removing the water from the acidified aqueous solution to yield a solid containing zosteric acid;

dissolving the solid containing the zosteric acid in methanol;

removing any undissolved solid from the methanol solution;

removing the methanol from the methanol solution to yield a solid containing zosteric acid;

dissolving the solid containing zosteric acid in water to form an aqueous solution containing zosteric acid;

passing the aqueous solution containing zosteric acid through a crosslinked, strongly basic anionic exchange resin in its hydroxyl form;

passing the aqueous solution containing the zosteric acid through a crosslinked, strongly acidic ion exchange resin; and removing the water from the aqueous solution containing zosteric acid to yield solid zosteric acid.

5. A method of claim 4, wherein the anionic exchange resin is 40–60 mesh resin 8–25% crosslinked with divinylbenzene and has a porosity of about 20–60% and wherein the cationic exchange resin is 40–60 mesh resin 10–20% crosslinked with divinylbenzene and has a porosity of about 20–60%.

6. A method of claim 4, further comprising, after the contacting step, the step of removing any undissolved solids from the aqueous solution containing zosteric acid.

7. A method of claim 4, wherein the steps of separating the aqueous phase from the organic phase;

removing the water from the aqueous phase to yield a solid containing the zosteric acid salt;

redissolving the solid containing the zosteric acid salt in-water to form an aqueous solution containing the zosteric acid salt; and acidifying the aqueous solution containing the zosteric acid salt to convert the zosteric acid salt to zosteric acid; are combined into the steps of:

separating the aqueous phase from the organic phase; and acidifying the aqueous phase containing the zosteric acid salt to convert the zosteric acid salt to zosteric acid.

8. A method of claim 4, wherein the anionic exchange resin and the cationic exchange resin are contained in a single column.

9. A method of claim 4, wherein the basic solution is extracted three-times with diethylether as the water-immiscible, polar organic solvent.

10. A method of claim 9, wherein the anionic exchange resin is 40–60 mesh resin 8–25% crosslinked with divinylbenzene and has a porosity of about 20–60% and wherein the cationic exchange resin is 40–60 mesh resin 10–20% crosslinked with divinylbenzene and has a porosity of about 20–60%.

11. A method for preparing zosteric acid comprising the steps of:

dissolving p-coumaric acid in pyridine to yield a solution;

adding chlorosulfonic acid to the pyridine solution;

allowing the p-coumaric acid and chlorosulfonic acid to react for a time and under conditions sufficient to form zosteric acid;

adding sufficient water to hydrolyze any remaining chlorosulfonic acid;

extracting the solution with a water-immiscible, polar organic solvent to yield an aqueous phase containing zosteric acid and an organic phase;

separating the aqueous phase containing zosteric acid from the organic phase;

adding an amount of a strong Brönsted base to the aqueous phase containing zosteric acid to neutralize the zosteric acid and form a basic solution containing the zosteric acid salt;

extracting the basic solution with an organic solvent to yield an aqueous phase containing the zosteric acid salt and an organic phase;

separating the aqueous phase containing the zosteric acid salt from the organic phase;

removing the water from the aqueous phase containing the zosteric acid salt to yield a solid containing the zosteric acid salt;

redissolving the solid containing the zosteric acid salt in water to form an aqueous solution containing the zosteric acid salt;

acidifying the aqueous solution containing the zosteric acid salt to convert the zosteric acid salt to zosteric acid;

removing the water from the acidified aqueous solution to yield a solid containing zosteric acid;

dissolving the solid containing the zosteric acid in methanol to form a methanol solution;

removing any undissolved solid from the methanol solution;

removing the methanol from the methanol solution to yield a solid containing zosteric acid;

dissolving the solid containing zosteric acid in water to form an aqueous solution containing zosteric acid;

passing the aqueous solution containing zosteric acid through a crosslinked, strongly basic ion exchange resin in its hydroxyl form;

passing the aqueous solution containing the zosteric acid through a crosslinked, strongly acidic ion exchange resin; and removing the water from the aqueous solution containing zosteric acid to yield solid zosteric acid.

12. A method of claim 11, wherein the anionic exchange resin is 40–60 mesh resin 8–25% crosslinked with divinylbenzene and has a porosity of about 20–60% and wherein the cationic exchange resin is 40–60 mesh resin 10–20% crosslinked with divinylbenzene and has a porosity of about 20–60%.

13. A method of claim 11, wherein the steps of separating the aqueous phase from the organic phase;

removing the water from the aqueous phase to yield a solid containing the zosteric acid salt;

redissolving the solid containing the zosteric acid salt in water to form an aqueous solution containing the zosteric acid salt; and acidifying the aqueous solution containing the zosteric acid salt to convert the zosteric acid salt to zosteric acid; are combined into the steps of:

separating the aqueous phase from the organic phase; and acidifying the aqueous phase containing the zosteric acid salt to convert the zosteric acid salt to zosteric acid.

14. A method of claim 11, wherein the anionic exchange resin and the cationic exchange resin are contained in a single column.

15. A method of claim 14, wherein the anionic exchange resin is a 40–60 mesh resin 8–25% crosslinked with divinylbenzene and has a porosity of about 20–60% and wherein the cationic exchange resin is a 40–60 mesh resin 10–20% crosslinked with divinylbenzene and has a porosity of about 20–60%.

16. A method of claim 11, wherein the reaction mixture is heated to a temperature ranging from about 60 to 70° C. and further comprising, after the reaction is complete, the steps of:

cooling the reaction mixture to at least room temperature;

adding an amount of a strong Brönsted acid to the reaction mixture to neutralize the pyridine and aniline and precipitate the zosteric acid; and collecting the precipitated zosteric acid.

* * * * *